(12) United States Patent
Mochida et al.

(10) Patent No.: US 7,821,529 B2
(45) Date of Patent: Oct. 26, 2010

(54) IMAGE PICKUP SYSTEM

(75) Inventors: Akihiko Mochida, Hino (JP);
Katsuyuki Saito, Sagamihara (JP);
Makoto Tsunakawa, Toda (JP); Noboru Kusamura, Hino (JP); Kotaro Ogasawara, Tokyo (JP); Hideki Tashiro, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/670,114

(22) Filed: Sep. 24, 2003

(65) Prior Publication Data

US 2004/0061776 A1 Apr. 1, 2004

Related U.S. Application Data

(63) Continuation of application No. PCT/JP02/02400, filed on Mar. 14, 2002.

(30) Foreign Application Priority Data

Oct. 10, 2000 (JP) ............................. 2000-309674

(51) Int. Cl.
*A62B 1/04* (2006.01)
(52) U.S. Cl. ........................................ 348/65
(58) Field of Classification Search ................... 348/65, 348/66, 67, 68, 69, 70, 71, 72, 73, 74, 75, 348/76, 565
See application file for complete search history.

(56) References Cited

U.S. PATENT DOCUMENTS 4,868,646 A * 9/1989 Tsuji ........................... 348/76

5,031,044 A * 7/1991 Canfield et al. ............. 348/565
5,040,068 A 8/1991 Parulski et al.

(Continued)

FOREIGN PATENT DOCUMENTS

EP 0984628 A1 3/2000

(Continued)

OTHER PUBLICATIONS

Supplementary European Search Report dated Nov. 13, 2009.

*Primary Examiner*—David Czekaj
(74) *Attorney, Agent, or Firm*—Scully, Scott, Murphy & Presser, P.C.

(57) ABSTRACT

To provide an image pickup system having CCDs 25 driven at different frequencies respectively which can drive each CCD 25 with a predetermined frequency if a detachable camera head (or electronic endoscope) 28 is used and also can process a signal processing clock of a video processing circuit 29 with one type of clock. A drive signal of the predetermined frequency supplied to the CCD is produced via a generating circuit CXO 155 in the video processing circuit 29, a frequency dividing circuit 132 and a timing generator (T.G.) 131. A CCD signal outputted from the CCD 25 is inputted to a line memory 139 in a floating circuit 135. As a writing clock (WCK) of the line memory 139, the one which is divided in the frequency dividing circuit 132 to a frequency in accordance with the CCD 25 to be used is used, and as a reading clock (RCK), the one of one type of frequency is used without regard to the CCD 25 to be used. Hence, it is possible to perform the signal processing of a secondary circuit 136 of the line memory 139 and following ones always with a common generating clock.

5 Claims, 9 Drawing Sheets

U.S. PATENT DOCUMENTS

| | | | |
|---|---|---|---|
| 5,124,789 A * | 6/1992 | Hiyama et al. | 348/74 |
| 5,196,928 A * | 3/1993 | Karasawa et al. | 348/65 |
| 5,206,714 A * | 4/1993 | Kim | 348/565 |
| 5,255,092 A * | 10/1993 | Loonen | 348/718 |
| 5,287,188 A * | 2/1994 | Saeger et al. | 348/565 |
| 5,339,105 A | 8/1994 | Iura et al. | |
| 5,412,478 A * | 5/1995 | Ishihara et al. | 348/72 |
| 5,541,651 A | 7/1996 | Iura et al. | |
| 5,614,943 A | 3/1997 | Nakamura et al. | |
| 6,466,256 B1 * | 10/2002 | Takahashi et al. | 348/71 |

FOREIGN PATENT DOCUMENTS

| | | |
|---|---|---|
| JP | 01-297044 | 11/1989 |
| JP | 4-186988 | 7/1992 |
| JP | 4-313984 | 11/1992 |
| JP | 6-78212 | 3/1994 |
| JP | 10-118032 | 5/1998 |
| JP | 11-47087 | 2/1999 |
| JP | 2000-083182 | 3/2000 |

* cited by examiner

FIG.12A
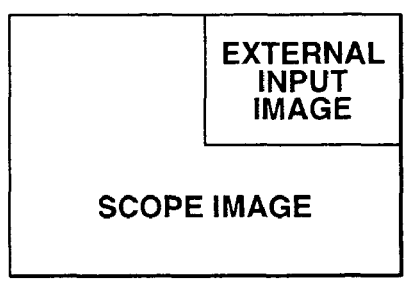
FIG.12D
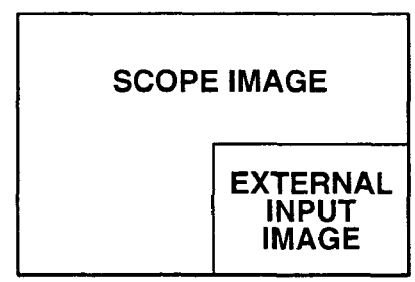
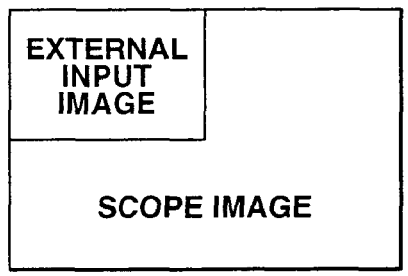
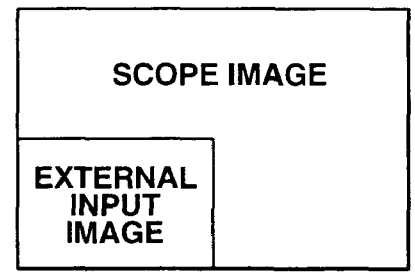
FIG.12B
FIG.12C

IMAGE PICKUP SYSTEM

CROSS REFERENCE TO RELATED APPLICATION

This application is a continuation application of PCT/JP02/02400 filed on Mar. 14, 2002 the disclosure of which is incorporated herein by its reference.

TECHNICAL FIELD

The present invention relates to an image pickup system having a feature in a control portion for a drive signal and an image pickup signal of a solid image pickup element such as CCD.

BACKGROUND ART

Recently, endoscope apparatus have been widely spread for performing observation and processing on an observed part by inserting an inserting portion to the observing part within a body cavity, for example, and by transmitting illumination light from an illumination light transmitting unit, such as a light guide fiber flux and irradiating it to the observing part from the distal end of the inserting portion so as to obtain an image of the observed part.

One of the endoscope apparatus is an electronic endoscope apparatus, which is provided with a solid image pickup element at the distal end of the inserting portion such as a CCD, forms an image of an observed part on an image pickup surface by using an objective optical system and converts it to electric signals. By performing signal processing on the electric signals, the image of the observed part can be displayed on a monitor, for example, and/or can be stored in an information recording device or the like as image data.

For example, in the field of surgery, there is provided a surgical rigid endoscope apparatus for displaying an image of an observed part on a monitor, for example, by inserting a rigid inserting portion of a rigid endoscope to the observed part within a body cavity or the like, transmitting illumination right by an illuminating light transmitting unit and irradiating it to the observing part from the distal end of the inserting portion, transmitting an image of the observed part to an ocular portion by using an image transmitting unit, such as a relay lens, from the distal end of the inserting portion and capturing the image of the observed part by using a CCD of an external TV camera, which is attached to the ocular portion removably.

For example, in Japanese Patent Application No. 11-182333, which was filed by the present applicant before, an image processing apparatus was disclosed for performing signal processing on an image signal by driving multiple kinds of CCD of the electronic endoscope apparatus or the surgical rigid endoscope apparatus.

In Japanese Unexamined Patent Application Publication No. 10-118032, a medical image display apparatus was disclosed for displaying on a monitor a main image and a sub-image in Picture-in-Picture.

However, in Japanese Patent Application No. 11-182333, processing is performed by synchronizing and driving drive clocks in all of the CCD's and by synchronizing signal processing clocks of a signal processing circuit. Yet, some CCD's can be driven only by a predetermined frequency. Thus, there is a problem that such a CCD cannot be used in some cases.

In Japanese Unexamined Patent Application Publication No. 10-118032, it is assumed that both main image and sub-image in Picture-in-Picture are images to be displayed on an entire area of a monitor as video images. In this case, a part of the image area of the main image cannot be viewed because of the sub-image. However, in an endoscope, a CCD is used in which an image is not displayed on an entire area of the monitor. A method has not been disclosed for using the area on the monitor effectively in that case.

The present invention is made in view of the above-described matters. It is an object of the present invention to provide an image pickup system, which can drive CCD's by using a predetermined frequency even when a camera head (or an electronic endoscope) using multiple kinds of CCD are used and which can perform a signal processing clock of a signal processing circuit by using one kind of clock.

It is another object of the present invention to provide an image pickup system, which can construct an image in Picture-in-Picture effectively in an endoscope for which an image is not displayed on an entire area of a monitor.

DISCLOSURE OF INVENTION

An image pickup system of the present invention having a first image pickup unit self-containing a first image pickup element that constitutes one image pickup surface by arranging a plurality of scanning lines having a first number of pixels, a second image pickup unit self-containing a second image pickup element that constitutes one imaged screen by arranging a plurality of scanning lines having a second number of pixels, which is more than the first number of pixels, and a camera control unit to which the first image pickup unit or the second image pickup unit are connected freely removably for signal processing, includes:

first drive signal output means provided in the first image pickup unit for outputting, to the first image pickup element, a first drive signal with a first frequency which can sequentially read every scanning line in image-captured signals for one screen image-captured on the image pickup surface of the first image pickup element;

first writing signal generating means provided in the first image pickup unit for generating a first writing signal with the first frequency which can sequentially write every scanning line in image-captured signals for one screen from the first image pickup element read by the first drive signal;

second drive signal output means provided in the second image pickup unit for outputting, to the second image pickup element, a second drive signal with a second frequency which can sequentially read every scanning line in image-captured signals for one screen image-captured on the image pickup surface of the second image pickup element;

second writing signal generating means provided in the second image pickup unit for generating a second writing signal with the second frequency which can sequentially write every scanning line in image-captured signals for one screen from the second image pickup element read by the second drive signal;

memory provided in the camera control unit for sequentially storing image-captured signals for one scan from a connected image pickup unit based on a writing signal from the connected image pickup unit;

reading means for reading image-captured signals for one scan, which is stored in the memory, with the second frequency; and video signal processing means provided in the camera control unit for performing video-signal processing on the image-captured signals read with the second frequency from the memory by using the reading means.

In addition, an image pickup system of the present invention includes: an image pickup element that constitutes one image pickup surface by arranging a plurality of scanning lines having a first number of pixels; a drive circuit for outputting, to the image pickup element, a drive signal with a first frequency for sequentially reading an image-captured signal captured on the image pickup surface of the image pickup element for every scanning line; a line memory having a memory capacity, which can store one scanning line of image-captured signals read from the image pickup element; a writing signal generating circuit for outputting a writing signal with the first frequency to the line memory and for writing the image-captured signal; a reading signal generating circuit for outputting a reading signal with a second frequency, which is higher than the first frequency, to the line memory and for reading image-captured signals stored in one scanning line; and a video signal processing circuit for performing video signal processing on the image-captured signals read with the second frequency from the line memory.

Furthermore, an image pickup system of the present invention includes:

a first image pickup unit self-containing a first image pickup element that constitutes one image pickup surface by arranging a plurality of scanning lines having a first number of pixels;

a first drive circuit provided in the first image pickup unit for outputting, to the first image pickup element, a first drive signal with a first frequency which can sequentially read, for every scanning line, image-captured signals for one screen image-captured on the image pickup surface of the first image pickup element;

a first writing signal generating circuit for generating a first writing signal with the first frequency, which can sequentially write, for every scanning line, image-captured signals for one screen from the first image pickup element read by the first drive signal;

a second image pickup unit self-containing a second image pickup element that constitutes one image-captured screen by arranging a plurality of scanning lines having a second number of pixels, which is more than the first number of pixels;

a second drive circuit provided in the second image pickup unit for outputting, to the second image pickup element, a second drive signal with a second frequency, which can sequentially read, for every scanning line, image-captured signals for one screen image-captured on the image pickup surface of the second image pickup element;

a second writing signal generating circuit provided in the second image pickup unit for generating a second writing signal with the second frequency, which can sequentially write, for every scanning line, image-captured signals for one screen from the second image pickup element read by the second drive signal;

a camera control unit to which the first image pickup unit or the second image pickup unit are connected freely removably, a line memory provided in the camera control unit for sequentially storing image-captured signals for one scanning line from a connected image pickup unit based on a writing signal from the image pickup unit connected to the camera control unit;

a reading circuit for reading image-captured signals for one scanning line, which are output and stored in the line memory with the second frequency; and a video signal processing circuit provided in the camera control unit for performing video-signal processing on the image-captured signals read with the second frequency from the line memory by using the reading circuit.

BRIEF DESCRIPTION OF THE DRAWINGS

FIG. 12A to FIG. 12D are a first diagram for explaining operations of the upstream processing circuit and the video processing circuit in FIG. 11;

BEST MODE FOR CARRYING OUT THE INVENTION

Embodiments of the present invention will be described below with reference to drawings.

First Embodiment

Figure 1:
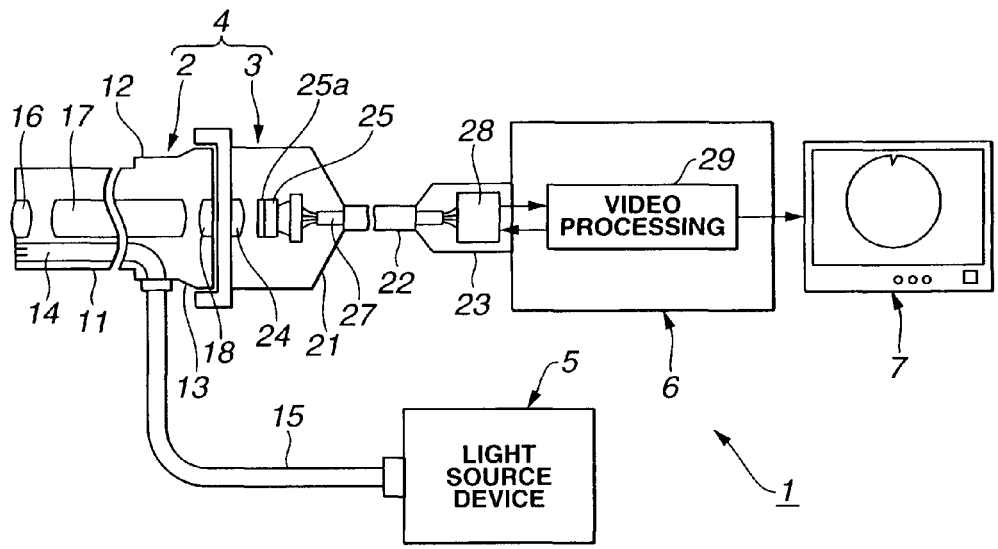
FIG. 1 is a configuration diagram showing a configuration of an endoscope apparatus relating to a first embodiment of the present invention.
Figure 2:
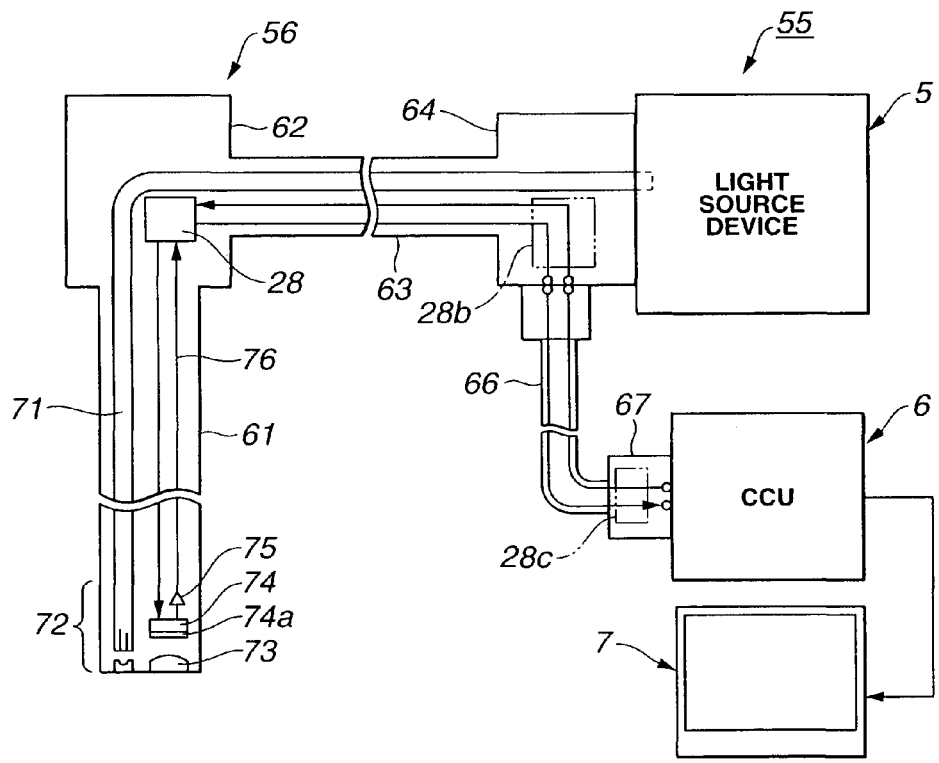
FIG. 2 is a configuration diagram showing a configuration of a modification example of the endoscope apparatus in FIG. 1.
Figure 3:
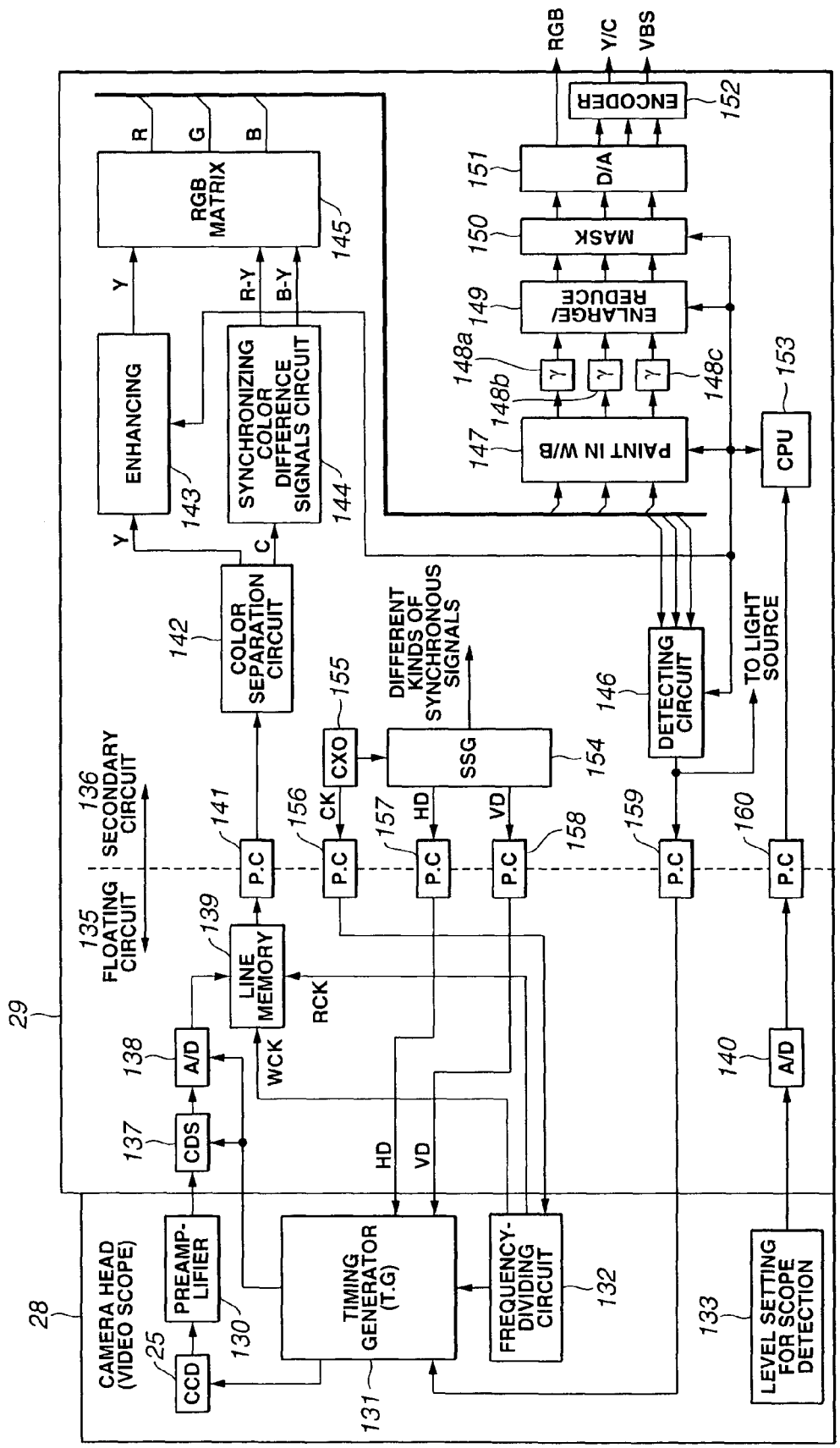
FIG. 3 is a block diagram showing a configuration of an upstream processing circuit and a video processing circuit.
Figure 4:
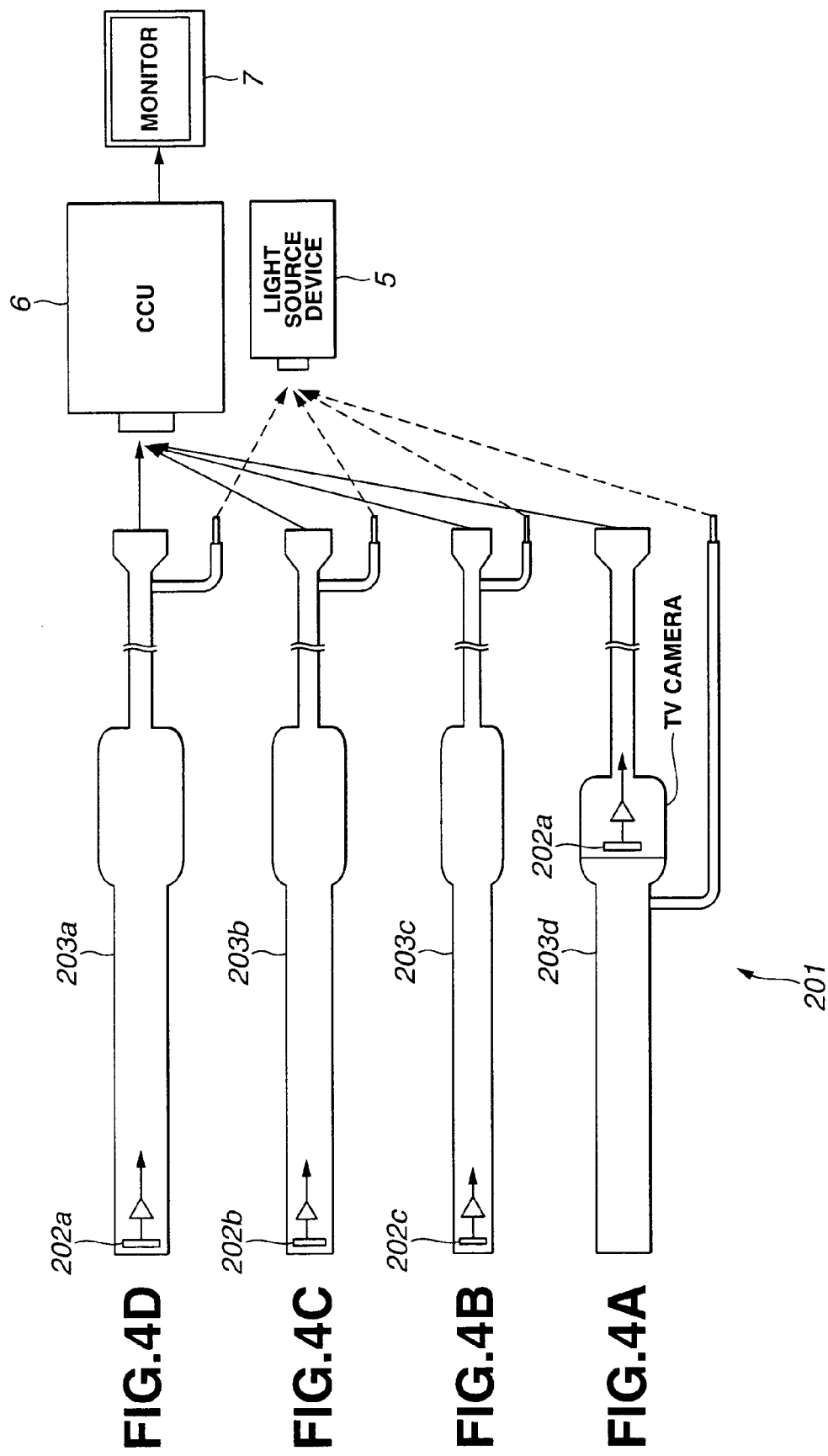
FIG. 4A to FIG. 4D are a first diagram for explaining operations of the upstream processing circuit and the video processing circuit in FIG. 3.
Figure 5:
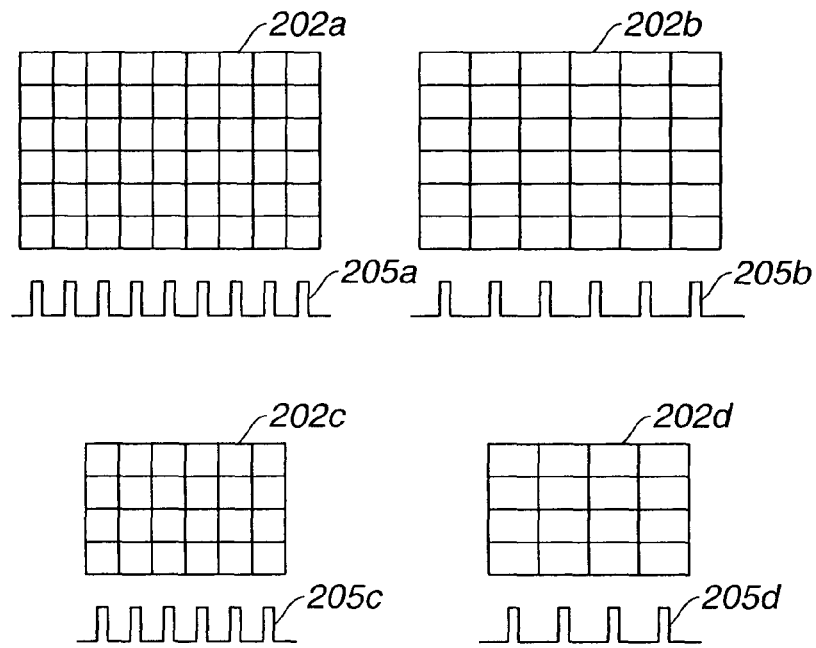
FIG. 5 is a second diagram for explaining operations of the upstream processing circuit and the video processing circuit in FIG. 3.
Figure 6:
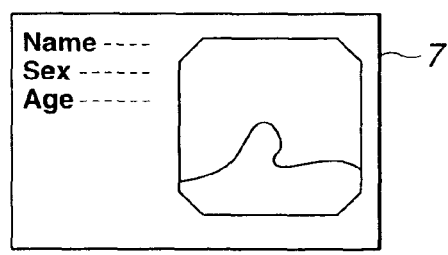
FIG. 6 is a third diagram for explaining operations of the upstream processing circuit and the video processing circuit in FIG. 3.
Figure 7:
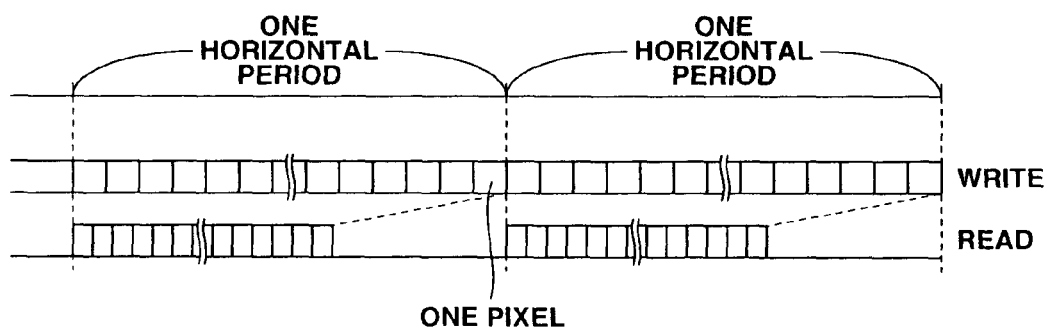
FIG. 7 is a fourth diagram for explaining operations of upstream processing circuit and the video processing circuit in FIG. 3.
Figure 8A:
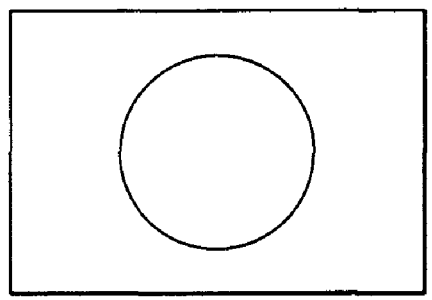
FIG. 8A and FIG. 8B are a fifth diagram for explaining operations of the upstream processing circuit and the video processing circuit in FIG. 3.
Figure 8B:
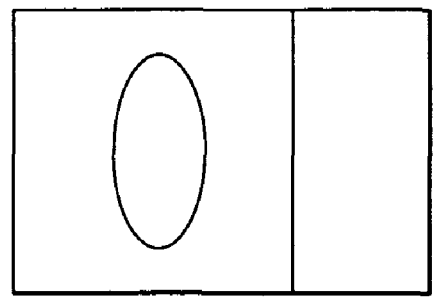
Figure 9:
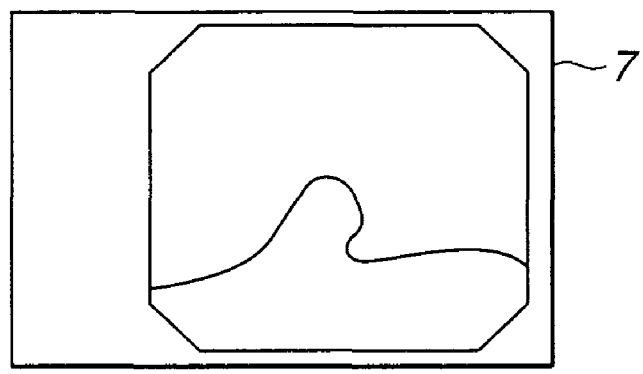
FIG. 9 is a sixth diagram for explaining operations of the upstream processing circuit and the video processing circuit in FIG. 3.
Figure 10:
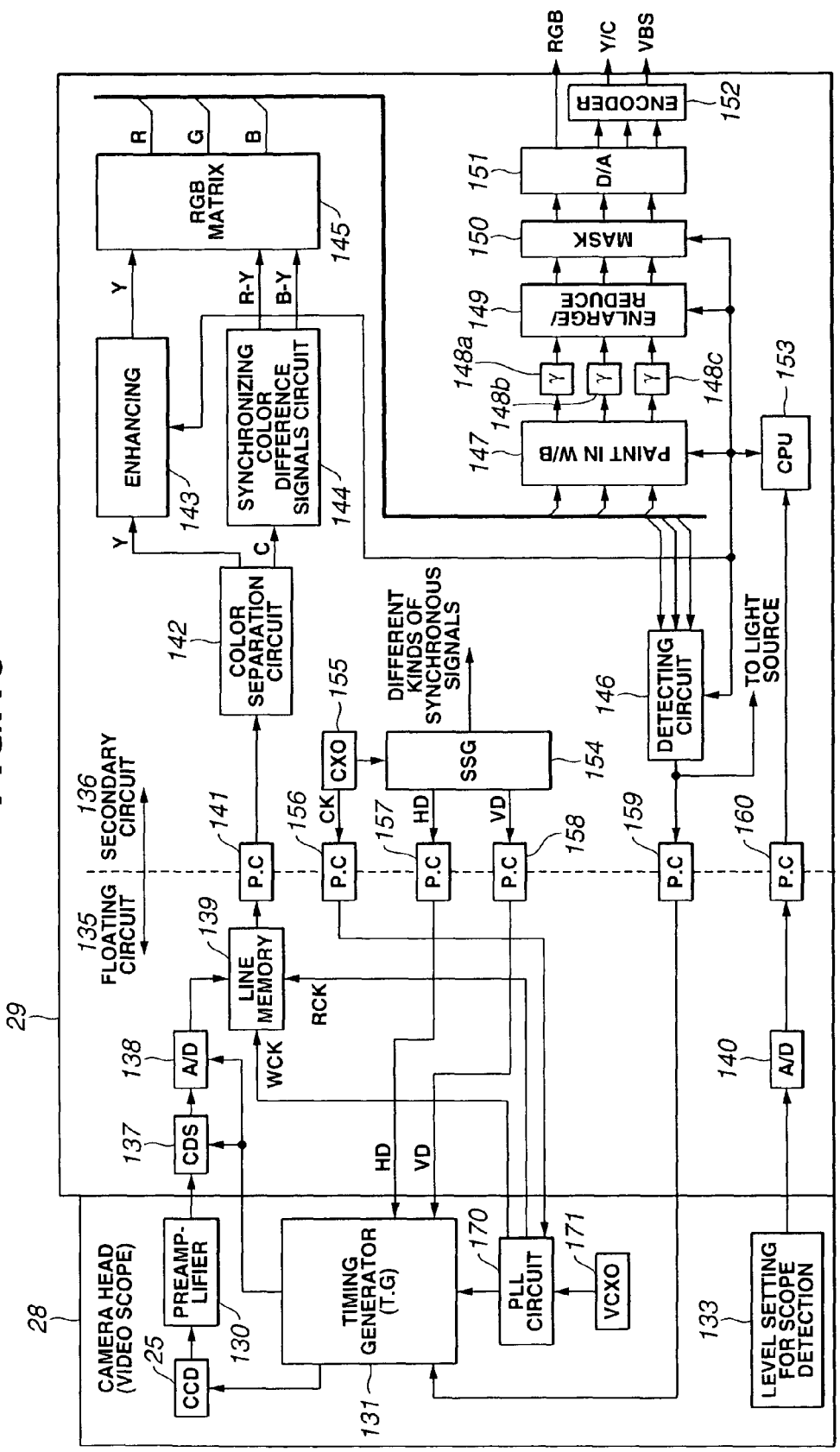
FIG. 10 is a block diagram showing a configuration of modification examples of the upstream processing circuit and the video processing circuit in FIG. 1.

FIGS. 1 to 10 relate to a first embodiment of the present invention. FIG. 1 is a configuration diagram showing a configuration of an endoscope apparatus; FIG. 2 is a configuration diagram showing a configuration of a modification example of the endoscope apparatus in FIG. 1; FIG. 3 is a block diagram showing a configuration of an upstream processing circuit and a video processing circuit; FIG. 4A to FIG. 4D are a first diagram for explaining operations of the upstream processing circuit and the video processing circuit in FIG. 3; FIG. 5 is a second diagram for explaining operations of the upstream processing circuit and the video processing circuit in FIG. 3; FIG. 6 is a third diagram for explaining operations of the upstream processing circuit and the video processing circuit in FIG. 3; FIG. 7 is a fourth diagram for explaining operations of upstream processing circuit and the video processing circuit in FIG. 3; FIG. 8A and FIG. 8B are a fifth diagram for explaining operations of the upstream processing circuit and the video processing circuit in FIG. 3; FIG. 9 is a sixth diagram for explaining operations of the upstream processing circuit and the video processing circuit in FIG. 3; and FIG. 10 is a block diagram showing a configuration of modification examples of the upstream processing circuit and the video processing circuit in FIG. 1.

[Construction]

As shown in FIG. 1, an endoscope apparatus 1 according to a first embodiment of the present invention includes an television camera external endoscope 4 (as an endoscope image pickup device) in which a television camera 3 having an image pickup unit is attached to an optical endoscope 2, a light source device 5 for supplying illuminating light to the optical endoscope 2, a camera control unit (abbreviated as CCU, hereinafter) connected to the television camera 3 freely removably for performing video signal processing for generating standard video signals, and a television monitor 7 for displaying video signals output from the CCU 6.

The optical endoscope 2 is a rigid endoscope having a rigid, for example, inserting portion 11, a grasping portion 12 provided at the back end of the inserting portion 11, and an ocular portion 13 provided at the rear end of the grasping portion 12.

A light guide 14 is inserted through the inside of the inserting portion 11. The light guide 14 is connected to the light source device 5 through a light guide cable 15, which is connected to a light guide end fitting of the grasping portion 12. Thus, white illuminating light is transmitted from a lamp, not shown, in the light source device 5 and is emitted from the distal end surface of the light guide 14. Then, a subject, such as an affected area, is illuminated.

An objective lens 16 is provided at the distal end portion of the inserting portion 11. An optical image of the subject is formed by the objective lens 16. The formed optical image is transmitted to a backward side of the inserting portion 11 through a relay lens system 17, for example, and can be observed through an ocular lens 18 provided in the objective portion 13.

The television camera 3 has a camera head 21 (externally) attached to the ocular portion 13 of the endoscope 2 freely removably, a camera cable 22 (as a signal transmitting system) whose proximal end is extended from the camera head 21, and a connector 23 provided at the end of the camera cable 22. The connector 23 is connected to the CCU 6 freely removably.

An image-forming lens 24 is provided in the camera head 21 by facing the ocular lens 18 of the endoscope 2. A charge-coupled element (abbreviated as CCD) 25 as a solid image pickup element is located at an image forming position of the image-forming lens 24. A mosaic filter 25a is located on a front surface of the CCD 25 for photoelectrically converting. The mosaic filter 25a color-separates a subject optically, which is conducted to the image pickup surface of the CCD 25.

A circuit substrate for forming a buffer amplifier, not shown, for example, is located on a back surface, for example, of the CCD 25. One end of (a signal cable 27 within) the camera cable 22 is connected to the CCD 25 and the circuit substrate. The other end is connected to an electric contact of the connector 23 through an upstream processing circuit 28 provided within the connector 23.

The processing circuit 28 is electrically connected to a video processing circuit 29 within the CCU 6 by connecting the connector 23 to the CCU 6. Then, the video processing circuit 29 outputs generated standard video signals to the television monitor 7.

This embodiment can be applied to a case of an electronic endoscope (video scope) having a solid image pickup element at the distal end portion, as shown in FIG. 2.

An endoscope apparatus 55 shown in FIG. 2 includes an electronic endoscope 56 self-containing an image pickup device, the light source device 5 for supplying illuminating light to the electronic endoscope 56, the CCU 6 for processing signals and generating video signals, and the television monitor 7 for displaying video signals output from the CCU 6.

The same reference numerals are given to the same components as those in the construction in FIG. 1.

The electronic endoscope 56 includes an inserting portion 61 to be inserted into a body cavity, an operating portion 62 provided such that an operator can hold a scope and on which switches, not shown, are mounted, a universal cable 63 whose proximal end is extended from the operating portion 62, and a connector portion 64 provided at the end of the universal cable 63. The electronic endoscope 56 is freely removably connected to the light source device 5 through a light guide end fitting extended to the distal end side of the connector portion 64.

A cable portion 66 is connected to the connector portion 64 and is freely removably connected to the CCU 6 through a connector 67 provided at the other end of the cable portion 66.

A light guide fiber 71 for transmitting illuminating light is inserted through the inside of the inserting portion 61 of the electronic endoscope 56. By connecting the light guide end fitting at the back end to the light source device 5, illuminating light is supplied from the light source device 5. The supplied illuminating light is transmitted and is emitted from the distal end surface of the light guide fiber 71 of the distal end portion 72 of the inserting portion 61 to a subject side, such as an affected area, further through an illuminating lens.

An objective lens 73 is provided to the distal end potion 72 of the inserting portion 61. A CCD 74 is located at an image-forming position of the objective lens 73. A mosaic filter 74a is provided on an image pickup surface of the CCD 74 for optical color-separation. A buffer amplifier 75 is provided at a signal output end of the CCD 74.

The CCD 74 is connected to the CCU 6 through a signal line 76 within the inserting portion 61, the operating portion 62 and the universal cable 63 and a signal line within the cable portion 66.

In the case of the electronic endoscope 56, there is a sufficient space in the operating portion 62. Thus, the upstream processing circuit 28 is provided within the operating portion 62. However, the upstream processing circuit 28 may be provided within the connector portion 64 as indicated by a reference numeral 28b and by a two-dotted line in FIG. 2. Alternatively, it may be provided within a monitor connector 67 as indicated by a reference numeral 28c.

Next, detail constructions of the upstream processing circuit 28 and the video signal processing 29 will be described by using FIG. 3.

Within the upstream processing circuit 28, there are provided a preamplifier 130 for amplifying CCD output signals, a timing generator 131 (abbreviated as TG, hereinafter) for supplying a drive signal to the CCD 25 and for supplying a sampling signal to a CDS and an A/D portion, which will be described later, and a frequency-dividing circuit 132 for frequency-dividing a clock supplied from the video processing circuit 29.

A scope detecting level output portion 133 is provided within the upstream processing circuit 28 for outputting a level for scope detection for specifying which CCD 25 the camera head 21 (or the electronic endoscope 56) uses.

The video signal processing circuit 29 within the CCU 6 includes a floating circuit 135 and a secondary circuit 136. Both of them are separated by insulating units such as photocouplers (P.C) 141, 156, 158, 159 and 160.

The floating circuit 135 includes a CDS circuit 137 for sampling video signals in the co-related dual manner and an A/D converting circuit 138 for A/D converting the output signals. The A/D conversion output is input to a line memory 139. Then, a reading frequency is converted by the line memory 139 through a reading clock (RCK), which is frequency divided in the frequency-dividing circuit 132.

An A/D converting circuit 140 for A/D converting scope-detecting analog signals from a scope-detecting level output portion 133 is provided within the floating circuit 135.

The secondary circuit 136 includes a color-separating circuit 142 for color-separating video digital signals transmitted in the P.C 141 into a brightness signal Y and a color difference signal C, an enhance circuit 143 for performing an edge enhancement processing on the color-separated bright signal, and a color-difference signal synchronizing circuit 144 for performing synchronizing processing on the color-separated color-difference signal and generating an R-Y signal and a B-Y signal. The enhancement-processed Y signal and R-Y and B-Y signals are input to the RGB matrix circuit 145 and are separated into RGB signals.

The separated RGB signals are input to a detecting circuit 146. A detecting signal for white balance control and a dimmer signal for controlling the light source device 5 and an electronic shutter are generated in the detecting circuit 146. The RGB signals are input to Paint-in-W/B circuit 147. Then, video white-balance processing and tone correcting processing are performed therein. After gamma processing is performed on the white-balancing processed RGB signals in gamma circuits 148a, 148b and 148c, they are input to an enlarge/reduce circuit 149. The RGB signals undergo image enlargement (or reduction) in the enlarge/reduce circuit 149, and an aspect ratio of the image is corrected.

The aspect-corrected video signals are masked at a part other than the image in a mask circuit 150 and then are converted to analog signals in a D/A converting circuit 151. The RGB output is output to the television monitor 7 as it is. A Y/C signal and a composite signal are generated in an encoder 152, which are output to the television monitor 7.

A CPU 153 is provided in the secondary circuit 136. The CPU 153 receives a scope detecting signal supplied from the A/D converting circuit 140 of the floating circuit 135 and switches processing of enhancement, RGB matrix, detecting circuit, white balancing, enlargement/reduction, masking and so on.

An SSG circuit 154 receives a clock signal from an oscillator 155 and generates different kinds of synchronizing signals and supplies a horizontal synchronizing signal (HD) and a vertical synchronizing signal (VD) to the floating circuit 135 through the P.C 157 and 158.

[Operations]

Next, operations of this embodiment will be described by using FIGS. 4A to 10.

As shown in FIGS. 4A to 4D, various types of camera head 21 and electronic endoscope 56 are connected to the CCU 6 in this embodiment. For the camera head 21 (or the electronic endoscope 56), several types of CCD 25 are used, as shown in FIG. 5. A CCD 202a is a high-pixel type of CCD 25. A CCD 202b is of a low-pixel type. A CCD 202c is of a high-pixel type, which cannot obtain a full-size image on the television monitor 7. A CCD 202d is a low-pixel type, which cannot obtain a full-size image on the television monitor 7.

An image of the camera head 21 (or electronic endoscope 56) using the CCD types 202c and 202d of the CCD's 25 is output to a part of the television monitor 7 as shown FIG. 6.

Since the CCD types 202a and 202b of the CCD's 25 are different from each other in a number of pixels in the horizontal direction, frequencies of drive signals are different as indicated by reference numerals 205a and 205b in FIG. 5. In this embodiment, these drive signals are generated in the upstream processing circuit 28. A CCD drive signals are generated in the TG 131 and the frequency-dividing circuit 132. An original oscillating clock (CK) generated in a CXO 155 is transmitted to the floating circuit through the P.C 156. The clock is transmitted to the upstream processing circuit 28 within the camera head 21 (or electronic endoscope 56) through a connector, not shown, and is input to the frequency dividing circuit 132. The frequency dividing circuit 132 generates drive clocks in accordance with types of CCD, respectively, provided in the camera head 21 (electronic endoscope 56).

For example, the CCD type 202a of the CCD 25 divides an original oscillating clock into two in the frequency-dividing circuit 132 and supplies them to the TG 131 since a drive clock is a two-division frequency of the original oscillating clock of the CXO 155. The CCD type 202b of the CCD 25 divides an original oscillating clock into three in the frequency dividing circuit 132 and supplies them to the TG 131 because of the three-dividing frequency of the original oscillating clock of the CXO 155.

The TG 131 generates CCD drive signals in accordance thereto, respectively, and supplies them to the CCD 25.

The CCD signals output from the CCD 25 are input to the line memory 139 through the preamplifier 130, the CDS 137, and the A/D 138. In the line memory 139, the clock conversion of the CCD signals is performed. A writing clock (WCK) for the line memory 139 is supplied from the frequency dividing circuit 132. A reading clock (RCK) is generated by dividing an original oscillating clock into two, which is generated in the CXO 155.

Next, writing and reading conditions for the line memory 139 in the case of the CCD type 202b of the CCD 25 will be described by using FIG. 7.

The line memory 139 is written and read and is reset for every one horizontal period. Writing is performed in a three-divided frequency of an original oscillating clock. Reading is performed in a two-divided frequency of an original oscillating clock. Thus, as shown in FIG. 7, reading ends in $\tfrac{2}{3}$ of one horizontal period. The remaining period becomes an idle transfer period.

Thus, signal processing of the secondary circuit in the line memory 139 and thereafter can be always performed by using a common original oscillating clock.

An output of the line memory 139 is input to the secondary circuit 136 through the P.C 141. The signal processing, as described above, is performed in the secondary circuit 136. The CPU 153 sets a level of the scope detecting level setting portion 133 and a type of the camera head 21 (or electronic endoscope 56) and a type of the CCD 25. In addition, the CPU 153 sets coefficients of enhancement, RGB matrix and white balancing.

Video signals having undergone the signal processing up to the gamma circuits 148a, 148b and 148c are input to the enlarge/reduce circuit 149.

In the enlarge/reduce circuit 149, an aspect ratio is corrected. In the CCD type 202a of the CCD 25, which is the high-pixel type, an image is not compressed, as shown in FIG.

8A, since the CCD drive frequency and a frequency of the signal processing in the secondary circuit 136 are the same. Here, the aspect ratio is not required to correct. Thus, the image is output as it is in the enlarge/reduce circuit 149.

In the CCD type 202b of the CCD 25, which is the low-pixel type, an image is compressed horizontally, as shown in FIG. 8B, since the frequency conversion is performed in the line memory 139. This is corrected here. In this embodiment, the drive frequency is a three-divided frequency of the original oscillating clock while a frequency for the signal processing in the secondary circuit is a two-divided frequency of the original oscillating clock. Therefore, by enlarging the image 3/2 times horizontally in the enlarge/reduce circuit 149, the aspect ratio is corrected.

Next, signal processing of the CCD types 202c and 202d of CCD 25 will be described.

The CCD type 202c of CCD 25 is the high-pixel type of CCD. Therefore, the drive frequency of the CCD is the same as that of the CCD type 202a of CCD 25. Since the CCD type 202d of CCD 25 is of the low-pixel type. Therefore, the drive frequency is the same as that of the CCD type 202b of CCD 25. Thus, the processing methods for the frequency conversion in the line memory 139 and for the aspect correction in the enlarge/reduce circuit 149 are the same as those for the CCD types 202a and 202b, respectively.

After the enlarge/reduce processing, those other than a video signal parts are masked in the mask circuit 150 as shown in FIG. 6, and superimposing text information and so on is performed.

Since the CCD types 202c and 202d of CCD 25 have an image only on a part of the television monitor 7 from the standard output, not only the correction of the aspect ratio but also enlargement of the image is performed in the enlarge/reduce circuit 149. Then, the enlarged image may be output as a standard, as shown in FIG. 9.

As shown in FIG. 10, a PLL circuit 170 and a VCXO 171 may be provided instead of the frequency-dividing circuit 132 such that drive clocks corresponding to respective CCD types may be generated.

[Effects]

According to this embodiment, the drawback that multiple operational frequencies are required for signal processing in accordance with types of CCD 25 in the conventional example is improved. A CCD drive signal is prepared in the camera head 21 (or electronic endoscope 56), and clock conversion is performed in the line memory. Thus, one type of clock signal processing can be performed within the CCU 6. Therefore, complicated signal processing in the CCU 6 can be prevented.

Second Embodiment

Figure 11:
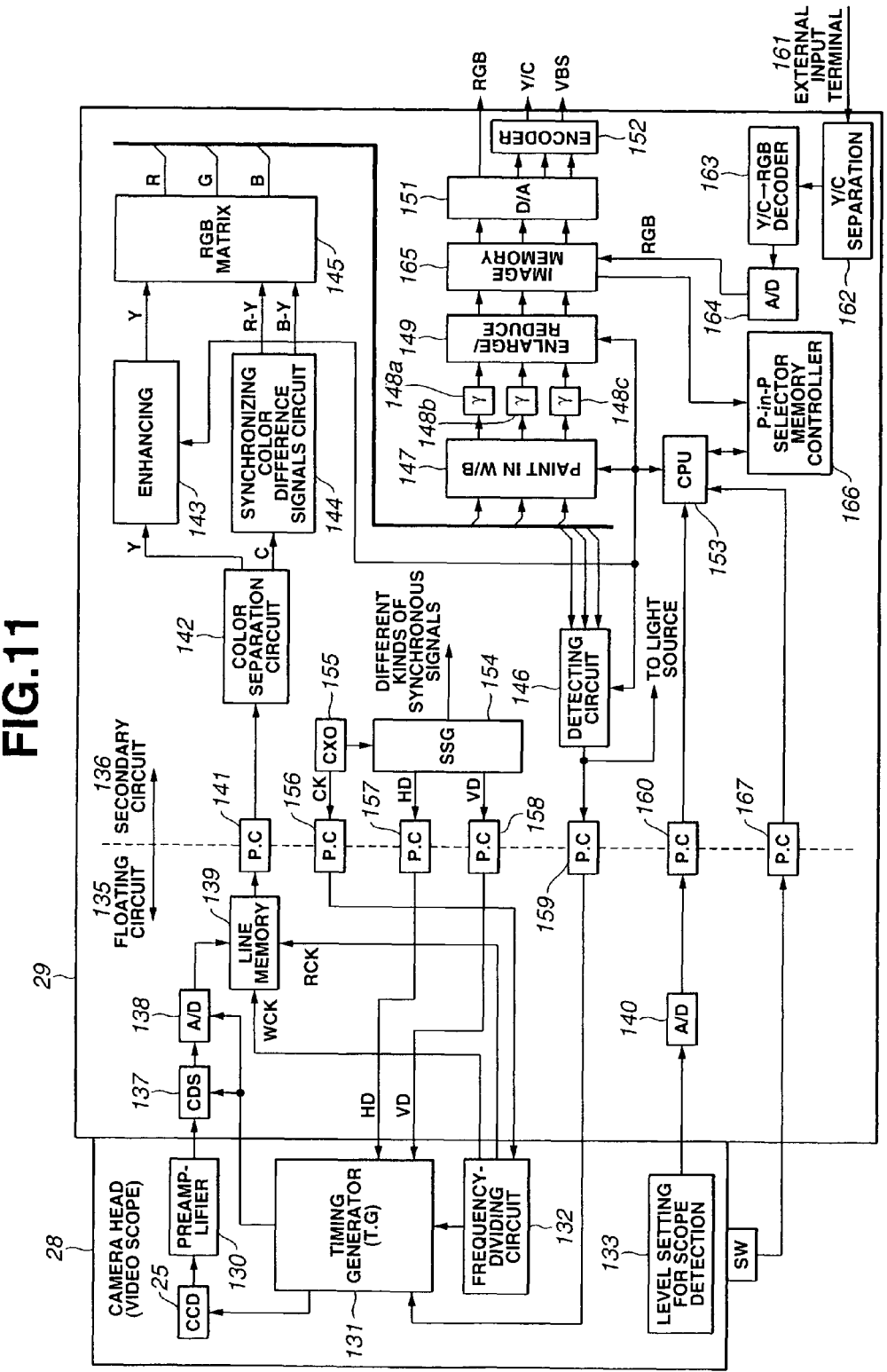
FIG. 11 is a block diagram of a configuration of the upstream processing circuit and the video processing circuit according to a second embodiment of the present invention.
Figure 13A:
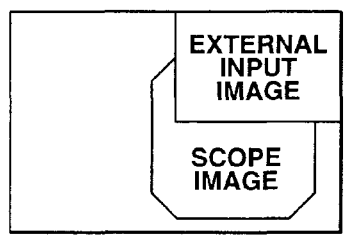
FIG. 13A to FIG. 13C are a second diagram for explaining operations of the upstream processing circuit and the video processing circuit in FIG. 11.
Figure 13B:
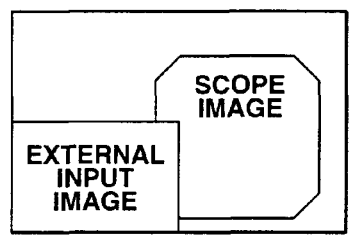
Figure 13C:
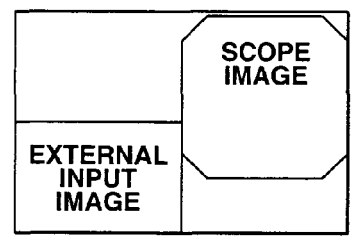
Figure 14:
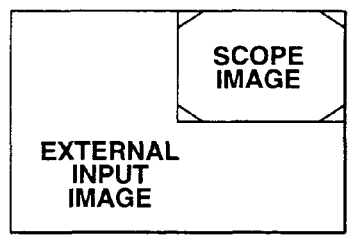
FIG. 14 is a third diagram for explaining operations of the upstream processing circuit and the video processing circuit in FIG. 11.

FIGS. 11 to 14 relate to a second embodiment of the present invention. FIG. 11 is a block diagram of a configuration of the upstream processing circuit and the video processing circuit according to the second embodiment of the present invention; FIG. 12A to FIG. 12D are a first diagram for explaining operations of the upstream processing circuit and the video processing circuit in FIG. 11; FIG. 13A to FIG. 13C are a second diagram for explaining operations of the upstream processing circuit and the video processing circuit in FIG. 11; and FIG. 14 is a third diagram for explaining operations of the upstream processing circuit and the video processing circuit in FIG. 11.

The second embodiment is mostly the same as the first embodiment. Thus, only different points will be described. The same reference numerals are given to the same components, and the description will be omitted.

[Configuration]

This embodiment has a terminal for inputting video signal from the outside. This is for achieving Picture-in-Picture (abbreviated as PinP, hereinafter) for inputting a video signal from a different video source such as an ultrasound endoscope and for displaying a sub-image including an externally input image on a main image including scope images as shown in FIG. 12.

As shown in FIG. 11, a composite signal input from an external input 161 is separated into a brightness signal and a color-difference signal in a Y/C separating circuit 162. Next, RGB signals are converted in the Y/C→RGB decoder 163. These signals are converted to digital signals in an A/D converting circuit 164 and then are recorded in an image memory 165.

Main video signals imaged by the camera head 21 (or electronic endoscope 56) also undergo the enlarge/reduce processing and then are recorded in a different area of the image memory 165.

A PinP selector memory control 166 is connected to the CPU 153 and selects video signals on the image memory 165 in accordance with a signal from the CPU 153.

[Operations]

Operations of this embodiment will be described by using FIGS. 12A to 14.

Also in this embodiment, multiple types of camera head 21 and electronic endoscope 56 are connected as shown in FIG. 4. For example, the camera head 21 and the electronic endoscope 56 shown in FIGS. 4A and 4B connect a full-screen display on the television monitor 7. Therefore, when external video signals are input thereto from the external input 161, the PinP display is obtained on the television monitor 7 as shown in FIG. 12A. The position of the sub-screen can be set by an SW 167 having push switch provided in the camera head 21 (or electronic endoscope 56). By pressing the SW 167, the position of the sub-screen is moved as FIG. 12A→FIG. 12B→FIG. 12C→FIG. 12D→FIG. 12A.

Next, a case will be described where external video signals are input to the external input terminal when the electronic endoscope 56 is connected as shown in FIGS. 4C and 4D. This screen disturbs an image on a main screen when a PinP image is set to position at the upper right part because it produces monitor display as shown in FIG. 13A. Conventionally, in this case, the position of the sub-screen is moved manually to a position where it does not disturb the main screen. In this embodiment, a type of the electronic endoscope 56 is determined based on a scope detecting signal obtained from the scope detecting level output portion 133. In this case, the position of the sub-screen is moved automatically as shown in FIG. 13B.

Also in the case of FIG. 13B, the sub-screen still disturbs the main screen to some extent, the main screen may be moved together as shown in FIG. 13C.

Furthermore, in this embodiment, a function may be provided for interchanging the main screen and the sub-screen in accordance with an operation of the SW 67. In this case, only a video signal part of an image of a scope, which moved toward the sub-screen as shown in FIG. 14 may be displayed excluding the masked area.

[Effect]

According to this embodiment, even in the case where an external input is adjusted for PinP, the externally input image can be displayed in the PinP manner at a proper position automatically without disturbing the image of the camera head 21 (or electronic endoscope 56).

The embodiments of the present invention have been described above. However, the present invention is not limited to the embodiments, but various changes can be given thereto naturally without departing the spirit of the present invention.

INDUSTRIAL APPLICABILITY

According to the present invention, as described above, the drawback that a CCD having a conventional technology cannot be driven with a predetermined frequency is overcome. In addition, since a signal processing clock of a CCU can be processed with one type of clock. Therefore, the circuit can be simplified.

The invention claimed is:

1. An endoscope imaging system comprising:
   an endoscope for photoelectrically converting an optical image of a subject and outputting an image-captured signal; and
   an image processing unit, to which the endoscope is detachably connected, for processing the image-captured signal from the endoscope,
   wherein the endoscope comprises:
      an image pickup element comprising one image-capture surface constructed with a plurality of scanning lines and driven by a pickup drive signal, wherein each of the plurality of scanning lines comprise a first number of pixels;
      a drive circuit for generating and outputting the pickup drive signal to the image pickup element, the pickup drive signal having a first frequency based on the first number of pixels for sequentially reading an image signal captured on the image-capture surface of the image pickup element for every scanning line; and
      a frequency dividing circuit for dividing a clock signal, having a preset frequency and being supplied by the image processing unit, to generate:
         a driving clock signal having the first frequency to be used by the drive circuit to generate and output the pickup drive signal,
         a writing signal having the first frequency for writing the image-captured signal read from the image pickup element to a line memory, and
         a reading signal having a second frequency higher than the first frequency for reading the image-captured signal from the line memory; and
   wherein the image processing unit comprises:
      the line memory having a memory capacity capable of storing one scanning line of image-captured signals read from the image pickup element;
      an oscillator for generating the clock signal having the preset frequency; and
      a video signal processing circuit for performing video signal processing on the image-captured signals stored in the line memory and read from the line memory with a reading signal at the second frequency.

2. The endoscope imaging system according to claim 1, wherein the video signal processing circuit provides an enlarge/reduce processing function for performing horizontal enlargement or reduction based on a ratio between the first frequency and the second frequency.

3. The endoscope imaging system according to claim 1, wherein the image processing unit further comprises:

superimposing means for superimposing an externally input image signal on an image-captured signal processed in the video signal processing circuit; and
superimposing position control means for controlling a superimposing position of the externally input image signal in coordination with the image pickup element.

4. An endoscopic imaging system comprising:
   an endoscope for photoelectrically converting an optical image of a subject and outputting an image-captured signal; and
   a camera control unit for processing the image-captured signal from the endoscope,
   wherein the endoscope comprises an image pickup system for imaging a subject, said image pickup system comprising:
      a first image pickup unit comprising:
         a first image pickup element comprising one image-capture surface constructed with a plurality of scanning lines, wherein each of the plurality of scanning lines comprises a first number of pixels;
         a first drive circuit for generating and outputting a first drive signal for the first image pickup unit to sequentially read each scanning line of an image captured by the one image capture surface of the first image pickup element, wherein the first drive signal oscillates at a first frequency correlated to the first number of pixels;
         a first frequency dividing circuit for dividing a clock signal having a preset frequency to generate and output a first clock signal at the first frequency, which is provided to the first drive circuit to generate the first drive signal; and
         a first writing signal generating circuit for generating and outputting a first writing signal using the first clock signal at the first frequency to sequentially write each scanning line of an image-captured by the one image capture surface of the first image pickup element, wherein the first writing signal oscillates at the first frequency of the first clock signal; and
      a second image pickup unit comprising:
         a second image pickup element comprising one image-capture surface constructed with a plurality of scanning lines, wherein each of the plurality of scanning lines comprises a second number of pixels, which is larger than the first number of pixels;
         a second drive circuit for generating and outputting a second drive signal for the second image pickup unit to sequentially read each scanning line of an image captured by the one image capture surface of the second image pickup element, wherein the second drive signal oscillates at a second frequency correlated to the second number of pixels;
         a second frequency dividing circuit for dividing the clock signal having a preset frequency to generate and output a second clock signal at the second frequency, which is provided to the second drive circuit to generate the second drive signal; and
         a second writing signal generating circuit for generating and outputting a second writing signal using the second clock signal at the second frequency to sequentially write each scanning line of an image-captured by the one image capture surface of the second image pickup element, wherein the second writing signal oscillates at the second frequency of the second clock signal;

wherein the camera control unit comprises:
- a line memory for sequentially storing image-captured signals for one scanning line of the first and second image pickup units in coordination with a corresponding one of the first and second writing signals connected to the camera control unit;
- a clock for generating a clock signal at said preset frequency for use by the first and second image pickup units;
- a reading circuit for reading image-captured signals for one scanning line which are output and stored in the line memory using the second frequency signal; and
- a video signal processing circuit for performing video-signal processing on the image-captured signals read from the line memory by the reading circuit using the second frequency signal; and wherein the camera control unit detachably connects to the endoscope.

5. The endoscope imaging system according to claim 4, wherein the image pickup system is provided in a first camera head for an endoscope, and the second image pickup system is provided in a second camera head for an endoscope.

* * * * *